US00PP31839P2

(12) United States Plant Patent
Fielding

(10) Patent No.: US PP31,839 P2
(45) Date of Patent: Jun. 2, 2020

(54) ***RANUNCULUS* 'ROCPEACH'**

(50) Latin Name: ***Ranunculus cortusifolius* x *asiaticus***
Varietal Denomination: ROCPEACH

(71) Applicant: John Fielding, London (GB)

(72) Inventor: John Fielding, London (GB)

( * ) Notice: Subject to any disclaimer, the term of this patent is extended or adjusted under 35 U.S.C. 154(b) by 0 days.

(21) Appl. No.: 16/501,916

(22) Filed: Jul. 2, 2019

(51) Int. Cl.
*A01H 5/02* (2018.01)
*A01H 6/72* (2018.01)

(52) U.S. Cl.
USPC ..... Plt./263.1

(58) Field of Classification Search
USPC ..... Plt./263.1
CPC ..... A01H 5/02; A01H 6/72
See application file for complete search history.

(56) References Cited

PUBLICATIONS

PLUTO Plant Variety Database Aug. 16, 2020. p. 1.*

* cited by examiner

*Primary Examiner* — Annette H Para
(74) *Attorney, Agent, or Firm* — Cassandra Bright

(57) ABSTRACT

A new and distinct *Ranunculus* cultivar named 'ROCPEACH' is disclosed, characterized by cold-hardy plants producing multiple peach-yellow flowers per stem. The new variety is a *Ranunculus*, useful as an ornamental plant or for cut flower production.

2 Drawing Sheets

Figure 1:
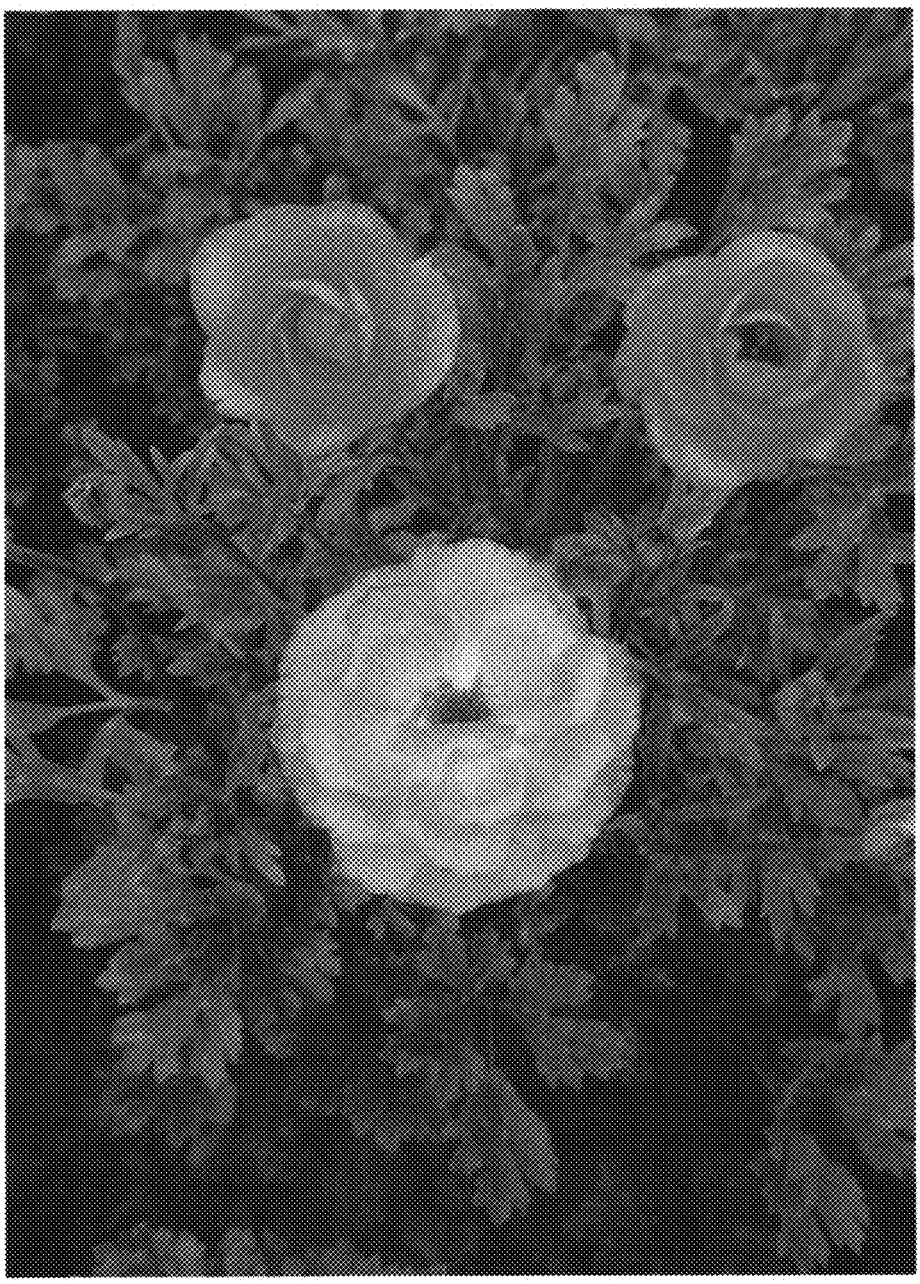

Latin name of the genus and species: *Ranunculus cortusifolius* x *asiaticus*.

Variety denomination: 'ROCPEACH'.

BACKGROUND OF THE INVENTION

The new *Ranunculus* cultivar is a product of a planned breeding program conducted by the inventor, John Fielding in London, United Kingdom. The objective was to produce varieties that are garden hardy in zone 8, and suitable for cut flower or garden uses. The cross resulting in this new variety was made in April of 2004.

The seed parent is an unnamed, unpatented variety of *Ranunculus cortusifolius*. The pollen parent is an unnamed, unpatented variety of *Ranunculus asiaticus*. The new variety was discovered in April 2009 by the inventor in a group of seedlings resulting from the 2004 crossing, in London, United Kingdom.

Asexual reproduction of the new cultivar was first performed by tissue culture in July 2009. The unique features of this cultivar are stable and reproduced true to type in more than 10 successive generations. Date of first sale of the new cultivar was Oct. 1, 2018, in the Netherlands.

SUMMARY OF THE INVENTION

The cultivar 'ROCPEACH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ROCPEACH' These characteristics in combination distinguish 'ROCPEACH' as a new and distinct *Ranunculus* cultivar:

1. Garden hardy in USDA Zone 7 or 8, has been observed to survive −15° Celsius in garden trials.
2. Can be used for cut flower or garden uses.
3. Cut flower will last in water for 12 to 14 days, with all flowers opening.
4. Branched stems with multiple flowers per stem.
5. Flower color is peach-yellow, with orange markings.

PARENT COMPARISON

Plants of the new cultivar 'ROCPEACH' are similar to plants of the seed parent, in most horticultural characteristics, however, plants of the new cultivar 'ROCPEACH' differ in the following:

1. The seed parent is taller than the new variety.
2. Flowers of the new variety are peach-yellow, while the seed parent's flowers are golden yellow.
3. The seed parent has 5 petals per flower, while the new variety has typically more than 85 petals.

Plants of the new cultivar 'ROCPEACH' are similar to plants of the pollen parent, in most horticultural characteristics, however, plants of the new cultivar 'ROCPEACH' differ in the following:

1. The pollen parent is shorter than the new variety.
2. The pollen parent is less winter hardy than the new variety.
3. The pollen parent has fewer flowers per stem than the new variety.

COMMERCIAL COMPARISON

Plants of the new cultivar 'ROCPEACH' are comparable to the unpatented commercial variety *Ranunculus* 'La Belle Champagne'. The two *Ranunculus* varieties are similar in most horticultural characteristics; however, the new variety 'ROCPEACH' differs in the following:

1. Plants of the new variety produce more flowers which are smaller in diameter than those of this comparator.
2. Flower color or the new variety is yellow with orange, colors present individually. Color of this comparator is yellow flushed with orange, as a solid single color.
3. The new variety is tolerant of more cold temperatures than this comparator.

BRIEF DESCRIPTION OF THE PHOTOGRAPHS

The accompanying photograph in FIG. 1 illustrates in full color flowering plants of the new variety at approximately 1 year old, grown outdoors.

Figure 2:
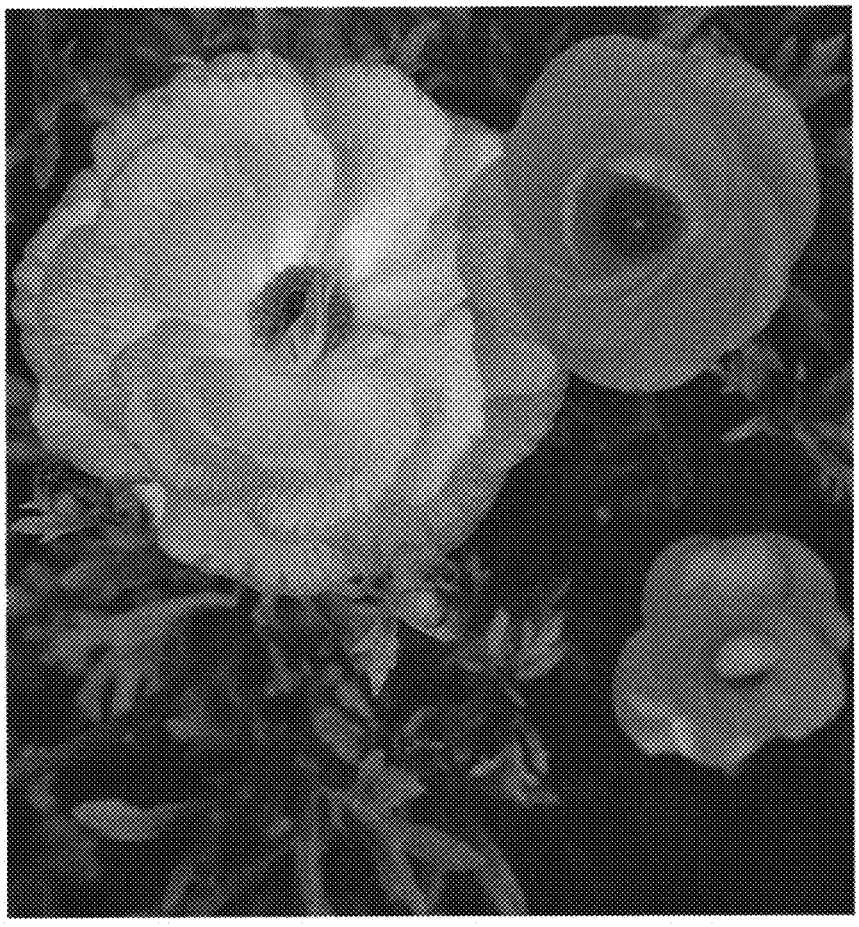

FIG. 2 illustrates a close-up view of flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 18-month-old 'ROCPEACH' plants grown in a vented, unheated polytunnel in London, United Kingdom. No chemical treatments were performed. The growing temperature ranged from 5° C. to 25° C. during the day and from −5° C. to 10° C. during the night. General light conditions are bright, normal sunlight. Measurements and numerical values represent averages of typical plant types. Botanical classification: *Ranunculus cortusifolius* x *asiaticus* 'ROCPEACH'.

PROPAGATION

Time to rooting: 15 days at approximately 10-15° C.
Time to produce a rooted plantlet: 20 days.
Root description: Secondary roots grow from the tuber and are fasciculate.

PLANT

Growth habit: Herbaceous perennial, robust, semi-erect.
Height to top flower: Average 65 to 75 cm.
Plant spread: Average 45 to 50 cm.
Growth rate: Medium to strong.
Branching characteristics: Branched panicle.
Length of lateral branches: Average range 15 to 40 cm.
Diameter of lateral branches: Average range 0.4 to 0.5 cm.
Texture of lateral branches: Glossy, slightly tomentose.
Internode length: Very close, forming basal rosette.
Strength of lateral branches: Medium.
Color of lateral branches: Near RHS Yellow-Green 144A.
Aspect/angle of branches: 30-35° from vertical.
Number of leaves per lateral branch: Usually 2.

FOLIAGE

Basal leaf:

*Arrangement.*—Young Leaf: Trifoliate. Mature Leaf: Biternate.
*Average length.*—20 to 40 cm.
*Average width.*—12 to 15 cm.
*Overall shape of blade.*—Young Leaf: Obovate. Mature Leaf: Palmatifid to palmatipartite.
*Dissected leaves, describe lobes, quantity of dissection.*—Leaves generally lobed, in 3 parts, each further divided in 3 or more lobes. Lobes become more pronounced as leaf ages.
*Apex.*—Young leaf: Rounded. Mature leaf: Acute.
*Base.*—Rounded.
*Attachment.*—Base of the plant.
*Margin.*—Dentate.
*Texture of top surface.*—Glabrous to slightly tomentose.
*Texture of bottom surface.*—Glabrous.
*Appearance of top surface.*—Slightly glossy.
*Appearance bottom surface.*—More glossy than upper surface.
*Leaf internode length.*—Very close to form a basal rosette.
*Color.*—Young foliage upper side: RHS Green NN137A to NN137B. Young foliage under side: RHS Yellow-Green 147B. Mature foliage upper side: RHS Green NN137B. Mature foliage under side: RHS Yellow-Green 147B.
*Venation.*—Type: Dichotomous; plunging into the limb at the upper surface; raised on the limb at the lower surface. Venation color upper side: RHS Yellow-Green 144B. Venation color under side: RHS Yellow-Green 144A.
*Petiole.*—Appearance: Long, tubular, rigid. Length: Average range 15 to 30 cm. Diameter: Average range 0.3 to 0.5 cm. Pubescence: Slightly tomentose. Color: RHS Yellow-Green 144B; base flushed Greyed-Red 181C to 182C.

Leaf at the nodes of the stems:

*Arrangement.*—Biternate.
*Average length.*—10 to 22 cm.
*Average width.*—12 to 16 cm.
*Overall shape of blade.*—Palmatipartite.
*Dissected leaves, describe lobes, quantity of dissection.*—Generally divided in 3 parts, each one of which is further divided in many deeply incised lobes.
*Apex.*—Acute.
*Base.*—Acute.
*Attachment.*—Petiolate.
*Margin.*—Entire to serrate.
*Texture of top surface.*—Glabrous to slightly tomentose.
*Texture of bottom surface.*—Glabrous.
*Appearance of top surface.*—Matte to slightly glossy.
*Appearance bottom surface.*—Slightly glossy.
*Leaf internode length.*—Average 5 to 18 cm.
*Color.*—Foliage upper side: RHS Green NN137A. Foliage under side: RHS Yellow-Green 146A.
*Venation.*—Type: Dichotomous, plunging into the limb at the upper surface and raised on the limb at the lower surface. Venation color upper side: RHS Yellow-Green 144A to B. Venation color under side: RHS Yellow-Green 144A.
*Petiole.*—Appearance: Long, slightly flat, rigid. Length: Average 2 to 9 cm. Diameter: Average 0.4 to 0.6 cm. Pubescence: Slightly tomentose. Color: RHS Yellow-Green 144A; Greyed-Purple 183B near attachment.

FLOWER

Bloom period: Spring.
Vase life (cut flower): 12 to 14 days in water.
Flower longevity on plant: 3 to 5 days from bud to open flower.
Persistent or self-cleaning: Self-Cleaning.
Bud:
*Closed bud*.—Shape: Broadly ovate with a sharp point. Length: 1 to 1.3 cm. Diameter: 1.2 to 1.4 cm. Color: RHS Yellow-Orange 14A at center; Yellow-Green 146A where sepals overlap.
*Slightly open bud*.—Shape: Flattened globular. Length: 1.3 to 1.5 cm. Diameter: 1.7 to 2.1 cm. Color: RHS Yellow-Green 144A.
Flower size:
*Diameter*.—6 cm.
*Height*.—4 cm.
Corolla: Round, regular.
Petals:
*Arrangement*.—Imbricated, disposed on the receptacle in very tight verticils. Size of petals variable, according to position, decreasing from exterior towards the center.
*Lobe length*.—2.6 to 3 cm.
*Lobe width*.—2.1 to 2.5 cm.
*Quantity*.—Numerous, more than 85.
*Texture*.—Silky, thin, resistant.
*Lobe apex*.—Rounded.
*Lobe shape*.—Obovate.
*Margin*.—Entire or finely crenate.
*Aspect*.—Concave with moderately reflexed apex when fully open.
*Color when opening*.—Inner surface: RHS Yellow 7A at base; fading to Orange 28B at apex. Outer surface: RHS Yellow 8B, flecked with Orange-Red N34C; Orange 25C near apex and margins.
*Color fully opened*.—Inner surface: Lower half RHS Yellow-Orange 16A fading to 14C in upper half; Yellow 7A at base. Outer surface: RHS Yellow 12C, flecked with N34D, tinted 28C.
Calyx/sepals:
*Quantity per flower*.—5 to 8.
*Shape*.—Concave, incurved at apex.
*Length*.—1.5 to 2.2 cm.
*Width*.—0.8 to 1 cm.
*Apex*.—Acute.
*Base*.—Flat.
*Margin*.—Entire.
*Texture*.—Lower surface: Tomentose. Upper surface: Tomentose.
*Color*.—Upper Surface: RHS Yellow-Orange 14A; White 155C near base. Lower Surface: RHS Green N138A; Yellow-Green 145D near base.
Peduncle: None.
Pedicel:
*Length*.—Average 17 to 25 cm.
*Diameter*.—Average 0.3 to 0.5 cm.
*Color*.—RHS Yellow-Green 144A.
*Orientation*.—Upright, straight, rigid.
*Pubescence*.—Slightly tomentose.
Fragrance: None.

REPRODUCTIVE ORGANS

Androecium:
*Stamens*.—Numerous, short and completely surround the gynoecium.
*Anther shape*.—Slightly curved.
*Anther length*.—Approximately 0.4 cm.
*Anther color*.—RHS Orange N25C.
*Pollen*.—Sparse.
Gynoecium: The pistils are numerous, short, locked together at the center of the corolla, dome-shaped apocarpous gynoecium.
*Height*.—0.8 cm.
*Width*.—0.6 cm.
*Shape*.—Domed, ovate.
*Pistil color*.—RHS Greyed-Purple 187B.

OTHER CHARACTERISTICS

Disease resistance: Typical for the species. Powdery mildew, leaf miner and rodent damage have all been observed in trials.
Drought tolerance and cold tolerance: More cold-hardy compared to other *Ranunculus* cultivars. Has survived −14° C. in trials in well-drained soil.
Fruit/seed production: Not observed.

What is claimed is:

1. A new and distinct cultivar of *Ranunculus* named 'ROCPEACH' as herein illustrated and described.

* * * * *